United States Patent
Vernengo et al.

(10) Patent No.: US 11,179,493 B2
(45) Date of Patent: Nov. 23, 2021

(54) METHODS AND COMPOSITIONS FOR INDUCING MULTI-TARGETED HEALING OF INTERVERTEBRAL DISC DEFECTS

(71) Applicant: ROWAN UNIVERSITY, Glassboro, NJ (US)

(72) Inventors: Andrea Jennifer Vernengo, Swedesboro, NJ (US); Thomas Richard Christiani, Williamstown, NJ (US); Cristina Iftode, Princeton, NJ (US); Jennifer Kadlowec, Haddon Township, NJ (US)

(73) Assignee: Rowan University, Glassboro, NJ (US)

( * ) Notice: Subject to any disclaimer, the term of this patent is extended or adjusted under 35 U.S.C. 154(b) by 155 days.

(21) Appl. No.: 16/090,086

(22) PCT Filed: Apr. 6, 2017

(86) PCT No.: PCT/US2017/026317
§ 371 (c)(1),
(2) Date: Sep. 28, 2018

(87) PCT Pub. No.: WO2017/176973
PCT Pub. Date: Oct. 12, 2017

(65) Prior Publication Data
US 2019/0117831 A1    Apr. 25, 2019

Related U.S. Application Data

(60) Provisional application No. 62/319,607, filed on Apr. 7, 2016.

(51) Int. Cl.
| | |
|---|---|
| A61L 27/20 | (2006.01) |
| A61L 27/16 | (2006.01) |
| A61L 27/52 | (2006.01) |
| A61L 27/58 | (2006.01) |
| A61L 27/54 | (2006.01) |
| A61L 27/50 | (2006.01) |

(52) U.S. Cl.
CPC .............. *A61L 27/20* (2013.01); *A61L 27/16* (2013.01); *A61L 27/50* (2013.01); *A61L 27/52* (2013.01); *A61L 27/54* (2013.01); *A61L 27/58* (2013.01); *A61L 2300/402* (2013.01); *A61L 2300/406* (2013.01); *A61L 2300/41* (2013.01); *A61L 2300/414* (2013.01); *A61L 2300/44* (2013.01); *A61L 2400/06* (2013.01); *A61L 2430/38* (2013.01)

(58) Field of Classification Search
CPC .......... A61L 27/16; A61L 27/20; A61L 27/50; A61L 27/54; A61L 27/58
See application file for complete search history.

(56) References Cited

U.S. PATENT DOCUMENTS

| | | |
|---|---|---|
| 2003/0023311 A1 | 1/2003 | Trieu |
| 2004/0220296 A1 | 11/2004 | Lowman et al. |
| 2005/0113923 A1 | 5/2005 | Acker et al. |
| 2007/0038300 A1 | 2/2007 | Bao et al. |
| 2007/0073402 A1 | 3/2007 | Vresilovic et al. |
| 2007/0093902 A1 | 4/2007 | Yuksel et al. |
| 2008/0076852 A1 | 3/2008 | Smith et al. |
| 2013/0184835 A1* | 7/2013 | Ferrari ................... A61L 27/16 623/23.61 |
| 2014/0056806 A1 | 2/2014 | Vernengo et al. |
| 2014/0219973 A1 | 8/2014 | Boyes et al. |

FOREIGN PATENT DOCUMENTS

WO       0240070 A2    5/2002

OTHER PUBLICATIONS

International Search Report and Written Opinion dated Jul. 3, 2017 for PCT International Application No. PCT/US2017/026317.

* cited by examiner

*Primary Examiner* — Edward J Cain
(74) *Attorney, Agent, or Firm* — Saul Ewing Arnstein & Lehr LLP; Domingos J. Silva; Paul A. Leicht

(57) ABSTRACT

The present disclosure relates to injectable compositions capable of forming a scaffold in situ at an intervertebral disc site, the composition comprising: (a) a biocompatible polymer; and (b) a biocompatible solvent system in sufficient amount to solubilize the biocompatible polymer in sufficient degree to allow injectable delivery to a disc site.

18 Claims, 4 Drawing Sheets

METHODS AND COMPOSITIONS FOR INDUCING MULTI-TARGETED HEALING OF INTERVERTEBRAL DISC DEFECTS

CROSS-REFERENCE TO RELATED APPLICATION

This application is a 35 U.S.C. § 371 national phase application of, and claims priority to, International Application No. PCT/US2017/026317, filed Apr. 6, 2017, which claims the benefit of priority under 35 U.S.C. § 119(e) to U.S. Provisional Application No. 62/319,607, filed Apr. 7, 2016, all of which are incorporated herein by reference in their entireties.

FIELD OF THE INVENTION

The present disclosure relates to novel compositions and methods for treatment of intervertebral disc degeneration that allow simultaneous repair of the annulus fibrosus and nucleus pulposus.

BACKGROUND

One of the major causes of lower back pain (LBP) is intervertebral disc degeneration caused by the dehydration of the central nucleus pulposus (NP) of the intervertebral disc (IVD). This process alters the biomechanics of the disc and eventually causes tears to form in the peripheral annulus fibrosus (AF). As a result, tissue fragments can pressurize nearby nerve roots, causing pain. Discectomy, a decompression procedure involving the surgical removal of the offending tissue fragments, such as NP or AF protrusions, that are impinging on nerve roots is the most common surgical procedure done to treat LBP, yet it is associated with inferior outcomes. Studies have shown as high as 34% of patients re-develop pain within 24 months and 19% require repeat surgery. This is attributable to the fact that discectomy does not restore healthy biomechanics to the disc, since tissue gaps will be filled with granulation tissue rather than healthy disc tissue. The degenerative cascade can therefore continue, and is reported to accelerate due to alterations made to the disc.

Tissue engineering with adipose-derived mesenchymal stem cells (AD-MSCs) is being investigated as treatment for disc degeneration and has been mainly focused on repairing the NP in early to mid-stages of degeneration, when the annulus is still competent. Recent in vivo animal studies on NP tissue engineering have shown low transplanted cell numbers post-implantation, potentially due to carrier expulsion from the disc space. Additional data has suggested that needle punctures can in fact accelerate disc degeneration.

Other studies in IVD tissue engineering focus on regenerating the NP with scaffold-encapsulated cells. However, one major consideration that has not been addressed in the current injectable NP tissue engineering strategies is that, in the short term, the needle puncture in the annulus can allow expulsion of the scaffold and, in the long term, it will accelerate degeneration. Conventional AF closure techniques such as sutures or plugs, failed to induce healing in a sheep model, or were expelled from goat and porcine models. Research on bioadhesive polymers with reactive groups has not been promising as it has shown limited biocompatibility and such bioadhesives have not supported long-term encapsulated cell survival and differentiation. Use of biocompatible fibrin sealants also suffers from significant limitations, as such the sealants have not been shown effective for IVD degeneration. Fibrin glues are unstable due to rapid degradation, thus making them non-ideal for the long repair process of the IVD. Their low mechanical properties also make fibrin glues inappropriate for load bearing, and they have a low cohesive strength. In addition, current tissue engineering strategies focus on the NP, yet the healthy biomechanics of the disc cannot be fully restored unless both the NP and AF are repaired. There is a need in the art for interventions that could be introduced into defects in both the NP and AF in order to reverse the condition and optimize clinical efficacy.

SUMMARY OF THE DISCLOSURE

The present disclosure relates to compositions that can be implanted into the intradiscal environment with minimal invasive procedures and through a small gauge needle. A tissue engineering-based approach is used to improve the current treatment for LBP with the development of a new method to replace and regenerate the portions of the disc removed during discectomy. In typical tissue engineering strategies for IVD repair, polymers seeded with autologous adipose derived mesenchymal stem cells (AD-MSCs) are injected into the intradiscal space to achieve formation of new tissue. Current clinical and pre-clinical data support the demand for improved methods for retaining the polymer in the disc space during motion and loading, thus localizing the transplanted cells as they regenerate tissue. In addition, current tissue engineering strategies focus on the NP, yet the healthy biomechanics of the disc cannot be fully restored unless both the NP and AF are repaired. Aspects of the present disclosure are directed to the development of a high strength adhesive that can be seeded with AD-MSCs and injected into defects in both the NP and AF of the IVD as a sealant, achieving multi-targeted healing of defects created by degeneration and/or discectomy. In this manner the present compositions provide a multi-targeted strategy for simultaneous repair of AF and NP by forming a scaffold matrix in situ.

The compositions described herein can be applied during discectomy, improving long-term outcomes of this procedure and resolving an unmet need in the current treatment of low back pain.

The presently described compositions can also enhance the clinical feasibility of NP regeneration strategies. Thus, a novel device is described to form a space-filling tissue engineering scaffold with adhesive properties that can stay anchored in the NP and AF of an IVD. To this end, the scaffold material described in the present disclosure can be applied in vivo in a single step to fill defects in the AF and NP.

In some aspects, the compositions of the present disclosure contain an acrylamide polymer such as poly(N-isopropylacrylamide) grafted with chondroitin sulfate (PNIPAAm-g-CS), and encapsulated alginate microparticles (MPs).

The injected material can localize encapsulated cells (AD-MSCs) by resisting expulsion due to its adhesive properties and support in situ site-specific differentiation of the cells toward AF or NP phenotypes.

Such IVD implants provide the first injectable scaffolds designed to be implanted in both NP and AF defects in a single step. The implants can also improve long-term outcomes of discectomy and enhance the clinical feasibility of NP regeneration strategies. Methods of treating intervertebral disc degeneration secondary to dehydration of the NP preferably employ the compositions containing an acrylamide polymer, such as poly(N-isopropylacrylamide) grafted with chondroitin sulfate (PNIPAAm-g-CS), and also containing encapsulated alginate microparticles (MPs) as adhesion mediators.

The compositions can be contained in kits useful for treating IVD as described above. Other aspects of the invention are also directed to methods of making the compositions. One aspect is directed to a composition capable of forming a scaffold in situ at a intervertebral disc site comprising (a) a biocompatible polymer at a concentration of from about 1 to about 90 weight percent based on the total weight of the composition; and (b) a biocompatible solvent system in sufficient amount to solubilize the biocompatible polymer in sufficient degree to allow delivery to a disc site, and further wherein the biocompatible polymer has a molecular weight and/or concentration sufficient to impart to the composition a viscosity that permits delivery to the disc site. The composition preferably has a suitable viscosity range for delivery at temperatures ranging from 1 to 40° C. The composition preferably has a migration distance ranging from 2 mm to 50 mm. The biocompatible solvent can be selected from the group consisting of water, ethanol, acetone and mixtures of any two or more thereof. The composition can further contain a contrast agent, which contrast agent can be a water insoluble contrast agent, such as those selected from the group consisting of tantalum, tantalum oxide, tungsten and barium sulfate. The biocompatible polymer of the composition is preferably selected from the group consisting of poly(ethylene oxides) (PEOs), poly(propylene oxides) (PPOs), copolymers of PEO and poly(lactic acid) (PLA), polyvinyl alcohol, acrylamides, polyurethanes, poly (N-vinyl-2-pyrrolidone), acrylates, copolymers of acrylates with N-vinyl pyrrolidone, N-vinyl lactams, polyacrylonitrile, polyglycolic acid, polyethylene terephthalate, polybutyl lactose, polycaprolactone, D-polylactic acid, L-polylactic acid, polyglytamic acid, poly-L-lysine, poly-L-aspartic acid, poly(N-isopropylacrylamide), and any mixtures of two or more thereof. Preferably the polymer is poly(N-isopropylacrylamide) which is further grafted with chondroitin sulfate (PNIPAAm-g-CS) and optionally contains alginate microparticles.

Another aspect is directed to a method of treating intervertebral disc defects comprising administering into the disc space of a mammal in need of such therapy a therapeutically effective amount of a composition, allowing in situ formation of a scaffold comprising a biocompatible polymer wherein the biocompatible polymer has a molecular weight and/or concentration sufficient to impart to the composition a viscosity that permits delivery to the disc site. The composition preferably comprises poly(N-isopropylacrylamide) grafted with chondroitin sulfate (PNIPAAm-g-CS). The composition can further contain encapsulated alginate microparticles (MPs) as adhesion mediators. The composition can further contain mesenchymal stem cells (MSC). The method simultaneously repairs defects of annulus fibrosus (AF) and nucleus pulposus (NP). The treatment preferably reduces the need to surgically remove NP tissues during the procedure by at least 300 mg.

A further aspect is directed to an intervertebral disc nucleus pulposus (NP) implant, comprising (a) a load-bearing body comprising a load-bearing hydrogel comprising poly(N-isopropylacrylamide) grafted with chondroitin sulfate containing alginate microparticles, the load-bearing body surgically implanted in an intervertebral disc space; and (b) an outer shell or plug formed in situ around said outer surface of said load-bearing body after the load-bearing body is implanted within the intervertebral disc space; wherein the outer shell or plug comprises an amount of biocompatible, biodegradable, elastic, and porous or partially porous material sufficient to substantially or completely cover the load-bearing body; wherein said outer shell or plug is a different and separable material, and where the outer shell or plug comprises a biocompatible, biodegradable, elastic, and porous or partially porous material that is injected partially or completely around the outer surface of said load-bearing body. Preferably the injected biocompatible material that forms said outer shell or plug is an adhesive material that allows nutrients to pass, and comprises a contrast agent. Preferably the load-bearing body comprises an elastic body sized to fill at least about 50%, or at least about 70%, or at least about 80%, or at least about 90%, or 100% of the intervertebral disc space into which the implant is desired to be implanted. The implant can further include a pharmacological agent, for example an agent comprising one or more members selected from the group consisting of contrast agents, growth factors for tissue regeneration, antibiotics, analgesics, anti-inflammatory drugs and steroids.

DETAILED DESCRIPTION OF PREFERRED EMBODIMENTS

Compositions

Figure 1:
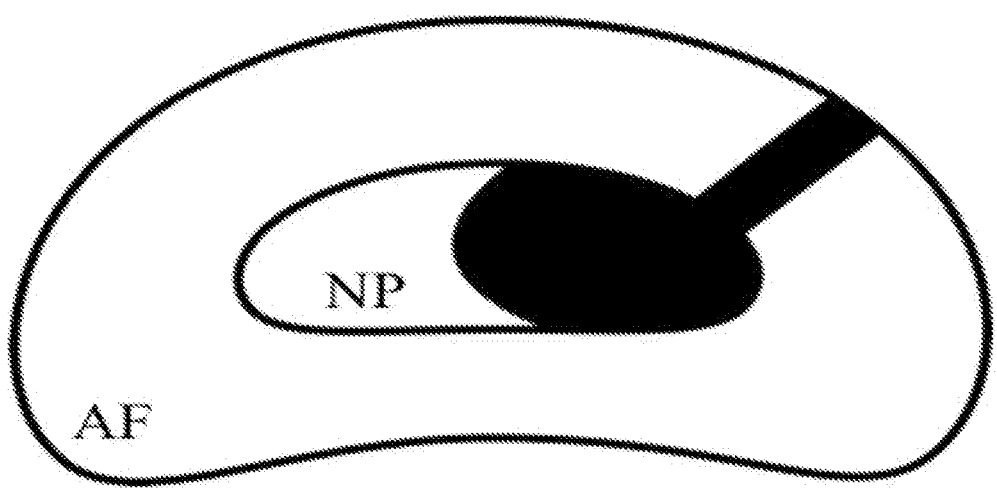
FIG. 1 presents a diagram of the injectable scaffold's design to fill defects in the annulus fibrosus (AF) and nucleus pulposus (NP) of the disc. The shaded area represents the tissue defects, created by degeneration or a nucleus replacement procedure.

FIG. 1 as depicted provides the filling of the defective area in shaded area during discectomy or during the implantation of a NP repair scaffold. Novel compositions are described herein that can be delivered to fill defective portions of intervertebral discs. The compositions contain a biocompatible polymer and a suitable solvent which allows delivery of the biocompatible polymer to the defective sections of the annulus fibrosus (AF) and nucleus pulposus (NP) of the disc.

The compositions are preferably in liquid form capable of forming a solidified matrix within the body of a mammal (e.g. a human) comprising a biocompatible polymer that exists in an extended form below a critical solution temperature (CST) that is lower than the normal body temperature of the mammal and in a condensed form at or above the CST. The composition can further contain an aminated component such as those selected from the group consisting of chondrotins, hyaluronates, keratins, alginates, celluloses, gums and dextrans.

The compositions can further include a biocompatible and/or biodegradable contrast agent allowing visualization of the delivery of the compositions to a disc site. The contrast agent can be a water insoluble contrast agent such as tantalum, tantalum oxide, tungsten and barium sulfate.

The ratio of polymer to solvent is preferably such that the composition exhibits at least 3, 4 or 5 fold increase in shear adhesive strength as compared to fibrin sealants which are currently the only adhesive scaffolds that have been investigated for IVD. Novel adhesive scaffolds are polymeric based and capable of forming a compact gel. Examples of suitable polymers are described in U.S. patent application Ser. No. 13/652,408 incorporated herein by reference in its entirety. The polymeric composition can contain polymers, homopolymers or oligomers including but not limited to poly(ethylene oxides) (PEOs), poly(propylene oxides) (PPOs), copolymers of PEO and poly(lactic acid) (PLA), poly(N-isopropyl acrylamides) (PNIPAAms), polyvinyl alcohol, acrylamides, polyurethanes, polyethylene glycol, poly(N-vinyl-2-pyrrolidone), acrylates, copolymers of acrylates with N-vinyl pyrrolidone, N-vinyl lactams, acrylamide, polyurethanes and polyacrylonitrile, polyglycolic acid, polyethylene terephthalate, polybutyl lactose, polycaprolactone, D-polylactic acid, L-polylactic acid, polyglytamic acid, poly-L-lysine, and poly-L-aspartic acid, and mixtures thereof. Such polymers can be grafted with chondroitin sulfate, and contain encapsulated alginate microparticles (MPs) as adhesion mediators. Exemplary compositions are poly(N-isopropylacrylamide) grafted with chondroitin sulfate (PNIPAAm-g-CS), and contain encapsulated alginate microparticles (MPs) as adhesion mediators. The term "encapsulated" as used herein with regard to the alginate MPs refers to a distribution of alginate MPs throughout the injectable polymer matrix. The distributed alginate MPs serve the function of increasing adhesion to the tissue and helping the polymer solution to stay in place during heating and solidification by increasing its viscosity.

The composition can further contain therapeutic agents or suitable cells to enhance clinical outcome. The therapeutic agent can include antibiotics, hydroxyapatite, anti-inflammatory agents such as corticosteroid or NSAIDs, analgesic agents, opioid pain killers, anesthetics such as lidocaine, bupivacaine, or the like, chemotherapeutic agents, bone morphogenic protein, demineralized bone matrix, collagen, growth factors such as insulin growth factor, basic fibroblast growth factor, platelet derived growth factor, calcium sulfate, immunosuppressants, fibrin, osteoinductive materials, apatite compositions, enzymes, proteins, hormones, and germicides.

Suitable cell types include those that can support in situ site-specific differentiation of the cells toward AF or NP phenotype. Such cell types include progenitor cells, fetal cells, stem cells, pulpous cells, autogenic bone marrow, mesenchymal stem cells (MSCs), such as adipose-derived mesenchymal stem cells (AD-MSCs).

The polymeric composition has a suitable viscosity at temperatures ranging from 1° C. to 40° C. to allow proper delivery in situ and further formation of the polymer such that, upon delivery to a vertebral site, it can form a scaffold capable of simultaneously repairing the defect in the annulus fibrosus (AF) and nucleus pulposus (NP) of the disc. The composition of the present disclosure has a viscosity ranging from 1 to 500 cSt at 1 to 40° C. The viscosity can also be suitable for a delivery at temperatures ranging from 2 to 25° C., or alternatively, the viscosity is suitable for a delivery at temperatures ranging from 2 to 5° C. The composition migrates a distance ranging from 2 mm to 50 mm. The composition can also migrate a distance of 2 to 40, or 2 to 30, or 2 to 25, or 2 to 20, or 5 to 50, or 5 to 40, or 5 to 30, or 5 to 25, or 5 to 20, or 10 to 30 mm. Alternatively, the composition migrates a distance of 2, or 5, or 10, or 15, or 20, or 25, or 30, or 35, or 40, or 45, or 50 mm.

The injectable polymer composition provides at least three (3), four (4) or preferably five (5) fold increases in shear adhesive strength. Preferably the shear strength of the injectable polymer composition having suspended MPs in sizes of more than 50, 60, 75, 90, 100, 105, and 125 μm was at least five (5) times greater than formulations with MPs smaller than 25, or smaller than even 20 μm.

An examplary injectable polymer based on PNIPAAm-g-CS containing alginate MPs exhibited a five-fold increase in shear adhesive strength compared to fibrin sealant, the only other adhesive scaffold investigated for IVD repair (2 kPa for fibrin versus ~10 kPa for the present example). The adhesive formulation composed of 5% (w/v) aqueous solution of PNIPAAm-g-CS with 50 mg/mL suspended MPs (105±39 μm) provided a significantly higher shear strength than the other formulations tested with smaller MPs (17±6 μm) or lower concentrations of MPs (25 mg/mL). PNIPAAm-g-CS+50 mg/mL of 105 μm MPs exhibited an almost five-fold increase in shear adhesive strength compared to the fibrin sealant used for cell-based IVD therapy.

Cytocompatibility was also observed with encapsulated adipose derived mesenchymal stem cells (AD-MSCs) for at least 5, 10, 14, 20, up to 30 days. The compositions remain localized during axial loading when implanted ex vivo into NP and AF defects in a porcine IVD, and such implantation restores range of motion to the intact condition in an ex vivo porcine model, after performing a partial nucleotomy following annulus injury. Those of ordinary skill in the art would appreciate that while other injectable scaffolds have been developed for NP replacement alone, the present disclosure describes the first biomaterial that is designed to be applied for the simultaneous regeneration of defects in the NP and AF. The inventive compositions provide a degree of adhesion such that the compositions will induce multi-targeted healing of IVD defects created by degeneration and/or discectomy.

Compositions are in injectable form which can be prepared in conventional forms, such as liquid solutions or suspensions, solid forms suitable for dissolution or suspension in a biocompatible liquid prior to injection, or as emulsions. The biocompatible liquid can be an aqueous or non-aqueous solution, such as water, alcohol, dimethyl sulfoxide, ethanol, acetone or combinations of any 2 or more thereof.

An intervertebral disc implant exemplary embodiment comprises (a) a load-bearing hydrogel composition comprising poly(N-isopropylacrylamide) grafted with chondroitin sulfate and optionally containing alginate microparticles, the load-bearing body being surgically implanted in an intervertebral disc space; and (b) an outer shell or plug formed in situ surrounding said load-bearing body after the load-bearing body is implanted within the intervertebral disc space; wherein said outer shell or plug comprises an amount of a biocompatible, biodegradable, elastic, and porous or partially porous material sufficient to substantially or completely cover and repair the load-bearing body and any other defective areas in the NP or AF. The outer shell or plug material is preferably injectable, and comprises an in-situ forming, in-situ crosslinking biopolymer, which possesses the mentioned properties of being biocompatible, biodegradable, and elastic, as well as being porous or partially porous with regard to allowing nutrients to pass into the intervertebral disc implant. The outer shell or plug material also preferably comprises a contrast agent. Exemplary biopolymers include polylactic acid (PLA), polyglycolic acid (PGA), polysaccharides such as cellulose, and cross-linked proteins such as collagen. The biocompatible material injected at the disc site is preferably an adhesive material in hydrogel form that contains suitable cell types such as progenitor cells, fetal cells, stem cells, pulpous cells, autogenic bone marrow, or mesenchymal stem cells, such as adipose-derived mesenchymal stem cells.

The term "substantially" as used herein indicates greater than 50%, or about 55% or greater, or about 60% or greater, or about 65% or greater, or about 70% or greater, or about 75% or greater, or about 80% or greater, or about 85% or greater, or about 90% or greater; preferably "substantially" indicates 90% or more. The term "completely" as used herein indicates about 95% or greater, or 96% or greater, or 97% or greater, or 98% or greater, or 99% or greater, or 100%; preferably "completely" indicates 100%. The term "partially" indicates about 50%, or about 55%, or about 60%, or about 65%, or about 70%, or about 75%, or about 80%, or about 85%, or about 90%. The term "about" generally means±10% of the value, but can also indicate ±5%, or alternatively ±1% of the specified value.

The injected biocompatible material is preferably a bioadhesive material. In various aspects the disc nucleus implant has an elastic body that is sized to fill at least about 50%, or 70%, or 80% or 90%, or 100% of the intervertebral disc space into which the implant is desired to be implanted. In various aspects the disc nucleus implant contains a pharmacological agent such as one or more members selected from the group consisting of contrast agents, growth factors, antibiotics, analgesics, and anti-inflammatory drugs, and steroids.

Methods of Making the Instant Compositions

The present disclosure is also directed to methods of forming a solidified matrix within the body of a mammal by suspending in an aqueous solvent a biocompatible thermally desolubilizable polymer wherein the polymer exists in an extended form below a critical solution temperature (CST) that is lower than the normal body temperature of the mammal and in a condensed form at or above the CST, and an aminated component of a mammalian extracellular matrix, wherein the aminated component is releasable within the body of the mammal and the polymeric component bears functional moieties capable of forming covalent bonds with both the aminated component and amine moieties at a tissue in the body of the mammal, and injecting the suspension into the body of the mammal at a disc space, wherein the polymer is transformed from its extended form to its condensed form thereby transforming to a solidified matrix at the disc site.

Further, methods of making adhesive scaffolding include providing a thermally sensitive polymer such as PNIPPAm, below its lower critical solution temperature (LCST) at 32° C., to form a miscible solution with water. Above the LCST, the solution becomes hydrophobic, so the polymer and water separate, forming a compact gel. Therefore, aqueous solutions of polymers such as PNIPAAm can be implanted via injection using an 18 gauge needle to form a space filling solid inside tissue defects in situ.

Glycosaminoglycans, preferably sulfated glycosaminoglycans such as the biopolymer chondroitin sulfate (CS) can be incorporated into the PNIPAAm matrix by covalent attachment to form a semi-synthetic hydrogel with the favorable mechanical characteristics of PNIPAAm and the enzymatic degradability, anti-inflammatory activity, water and nutrient absorption of CS.

Alginates such as sodium or calcium alginates can be added to the system to act as the adhesion mediator. For example, calcium-crosslinked alginate microparticles are added to the polymer solution as the adhesion mediators for the system. The microparticles are suspended in aqueous PNPAAm-g-CS solutions at room temperature and become entrapped or encapsulated in the gels formed at body temperature, creating a MP/hydrogel composite. Alginate MPs have been most commonly used for controlled drug delivery applications. However, in the current disclosure, the alginate MPs are incorporated because they significantly enhance the adhesive properties of PNIPAAm-g-CS.

Alginate in spherical MP form imparts the highest adhesive characteristics to the polymer, as opposed to using alginate in soluble form or in other particle geometries, like fibers. Moreover, formulations comprised of higher concentrations of MPs or larger MPs showed significantly higher shear strength than the formulations with smaller MPs or lower concentrations.

Suitable cell types such as mesenchymal stem cells can be added to the system prior to the local delivery. In one example, adipose derived mesenchymal stem cells (AD-MSCs) were suspended in room temperature PNIPAAm-CS solutions and delivered locally to the tissue upon implantation. AD-MSCs were shown to differentiate toward NP and AF phenotypes once in situ. The AD-MSCs embedded in the scaffold stay localized within the tissue defects during loading and develop a site-specific phenotype in vivo, depending whether the targeted tissue is the NP or AF.

Injectables can be prepared in conventional forms, either as liquid solutions or suspensions, solid forms suitable for dissolution or suspension in a biocompatible liquid prior to injection, or as emulsions. Biocompatible solvents can be any one of water, alcohol, dimethylsulfoxide, ethanol, acetone or any combinations thereof.

The scaffold as described herein is a considerable improvement over other materials that have been studied for regeneration of the IVD. The adhesive has higher mechanical properties and a longer degradation time than fibrin glue, while also demonstrating biocompatibility with encapsulated cells.

The disclosure also relates to a kit for making the liquid compositions. The kit includes 1) a biocompatible polymer in a dehydrated form, wherein the polymer exists at a temperature below the respective CST and lower than the normal body temperature of the mammal or above the CST, 2) the aminated component and c) optionally a biocompatible solvent.

Therapeutic Applications

Some aspects are directed to a method for detecting IVD, preferably IVD caused by dehydration of the central NP. The method can include the step of further providing a therapeutic strategy by administering to the patient in need of such therapy an effective amount of a composition that can facilitate healing process. Therapeutically effective amounts of the compositions are injected into the disc space. The term "therapeutically effective amount" is defined herein as a quantity of the composition which when administered to a subject, is sufficient to result in a clinically significant and measureable improvement in the subject's condition.

Other aspects of the present disclosure are directed to methods of treating disc degeneration by administering inventive scaffold compositions to the subject in need and allowing in situ formation of the biopolymers. Preferably the scaffold compositions contain poly(N-isopropylacrylamide) grafted with chondroitin sulfate (PNIPAAm-g-CS), and contain encapsulated alginate microparticles (MPs) as adhesion mediators. The composition can further contain MSC.

Discectomy is a decompression procedure involving the removal of the portions of the NP or AF that are causing pressure on the nerve root and causing back pain. Despite lumbar discectomy rates increasing worldwide, the surgery is associated with inferior outcomes and as high as 19% of the patients require future surgery. This is attributable to the fact that discectomy does not restore the healthy biomechanics to the disc, since tissue defects will be filled with granulation tissue, rather than healthy disc tissue. The degenerative cascade can therefore continue, and is reported to accelerate due to alterations made to the disc. The inventive methods of treating NP and AP minimizes the need to remove NP tissues during surgical procedures such as nulecotomy, resulting in significant increase in Range of Motion (ROM). The amount of NP tissue to be removed can be less than 500, 450, 400, 350 or preferably less than 300 mg causing ROM to significantly increase.

Other aspects provide a technology to replace or regenerate the portions of the disc removed during discectomy.

Other aspects further provide an effective method for plugging and inducing healing of a de novo annulus defect which makes NP regeneration clinically feasible.

Other aspects are directed to a method for enhancing the formation of a solid, non-migratory coherent mass that can be formed in situ to enhance regeneration of defective NP and AN in the disc of a mammal.

In other aspects, the therapeutic method of the present disclosure comprises: (a) placing a delivery device having an ejection port at a selected intervertebral disc in a mammal; (b) delivering through the ejection port of the delivery device a composition comprising a biocompatible polymer and a biocompatible solvent having suitable viscosity for easy delivery to the site, and (c) allowing the composition to form a scaffold in situ. In other aspects, the composition delivered comprises a biocompatible polymer at a concentration of from about 1 to 95 weight percent, preferably between 2 to 85, or 5 to 60 weight percent. Preferably the composition forms a PNIPAAm matrix by covalent attachment to form a semi-synthetic hydrogel with the favorable mechanical characteristics of PNIPAAm and the enzymatic degradability, anti-inflammatory activity, water and nutrient absorption of CS.

Other aspects are directed to use of implants for treatment of vertebral disc injury by placing an intervertebral disc nucleus pulposus implant that contains a load-bearing hydrogel comprising poly(N-isopropylacrylamide) grafted with chondroitin sulfate and optionally containing alginate microparticles, having an outer surface, where the load-bearing body is implanted, preferably by injection but implantation can also be achieved surgically, into an intervertebral disc space. The implant further contains an outer shell or plug formed in situ around the outer surface of the load-bearing body after the load-bearing body has been implanted within the intervertebral disc space. Preferably the outer shell or plug contains a contrast agent to assist in visualization during the procedure.

EXAMPLES

Novel Adhesive Scaffold for the NP and AF Composed of PNIPAAm-g-CS and Alginate MPs
Material and Methods Adipose-derived mesenchymal stem cells were purchased from the American Type Culture Collection (ATCC) and were used in the in vitro studies that established the biocompatibility of the MP/hydrogel composite.

An adhesive based on poly(N-isopropylacrylamide) grafted with chondroitin sulfate (PNIPAAm-g-CS), containing encapsulated alginate microparticles (MPs) as adhesion mediators was prepared. The system forms a free-flowing solution in water at room temperature and a space-filling gel at physiological temperatures. PNIPAAm-g-CS was synthesized via redox polymerization.

Calcium chloride particles of various size ranges were produced via an oil-in-water emulsion. MP size was manipulated by varying the emulsion stir speed and the emulsion to surfactant volume ratio.

Using this method, two MP size ranges were produced, small ($17\pm6$ μm) and large ($105\pm39$ μm). To prepare the adhesive, small and large microparticles were suspended at a concentration of either 25 or 50 mg/mL in 5% (w/v) solution of PNIPAAm-g-CS in phosphate buffered saline (PBS) at room temperature.

In Vitro Characterization of Adhesive Strength.

Adhesive properties in contact with porcine AF tissue were tested in shear with a fixture designed and fabricated by our group. Shear testing was chosen to screen formulations in vitro because it is akin to the likely mode of failure in an IVD if the hydrogel were extruded through the annulus due to insufficient adhesion. A test method was developed based on ASTM standard F 2255-05.

Figure 2:
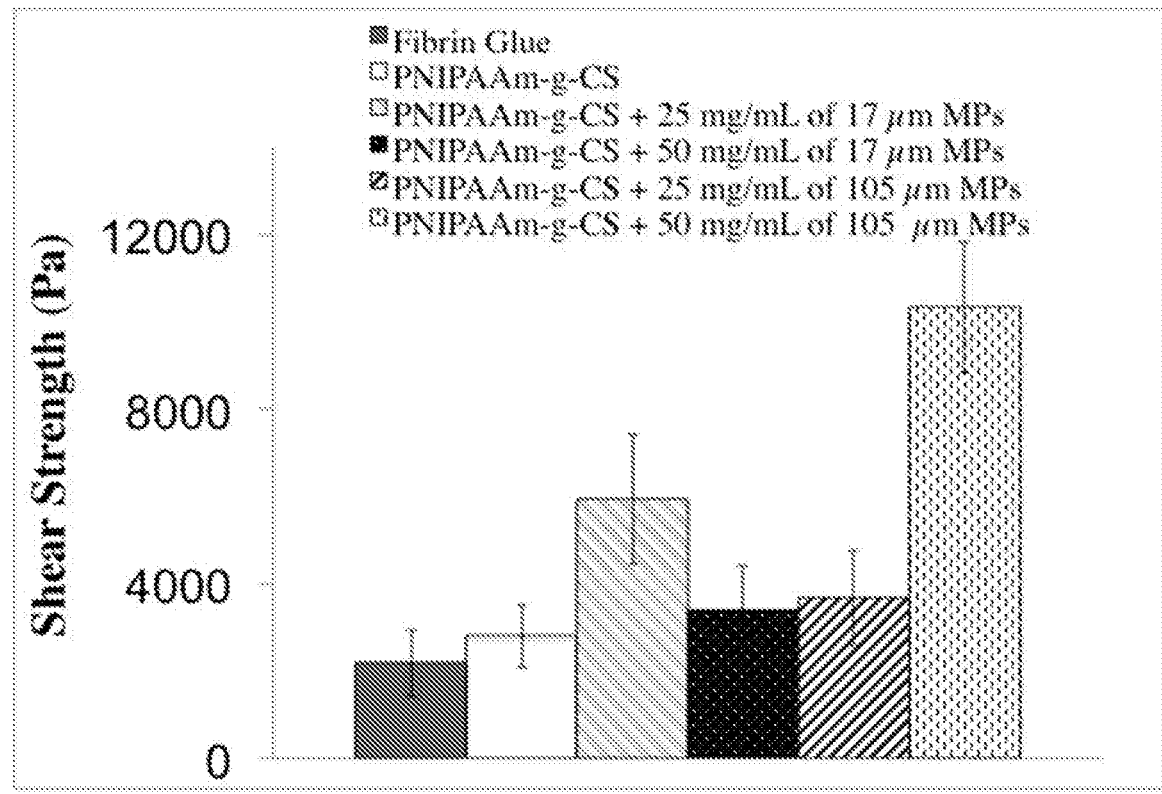
FIG. 2 presents a graph of the shear adhesive strength of PNIPAAm-g-CS formulations containing varying microparticle (MP) concentration (25 or 50 mg/mL) and size (17 or 105 In).

Two samples of AF tissue were cut to dimensions 5 mm×10 mm, affixed to plexiglass slides with cyanoacrylate adhesive and warmed to 37° C. in a saline bath. Next, 60 μL of "PNIPAAm-g-CS+MPs" or EVICEL® fibrin sealant (control) was applied to the samples by pipette and allowed to solidify for 5 minutes. The AF tissue samples were displaced relative to one another using an FGS-200PV E-Force Test Stand at a rate of 5 mm/min until the hydrogel failed in shear, while displacement and force were recorded. The data in FIG. 2 shows that the adhesive formulation composed of 5% (w/v) aqueous solution of PNIPAAm-g-CS with 50 mg/mL suspended MPs ($105\pm39$ μm) has significantly higher shear strength than the other formulations tested with smaller MPs ($17\pm6$ μm) or lower concentrations of MPs (25 mg/mL). PNIPAAm-g-CS+50 mg/mL of 105 μm MPs exhibited an almost five-fold increase in shear adhesive strength compared to the fibrin sealant, which is the only other injectable adhesive that has been studied for cell-based IVD therapy.

Cellular Viability and Differentiation In Vitro.

Figures 3A, 3B:
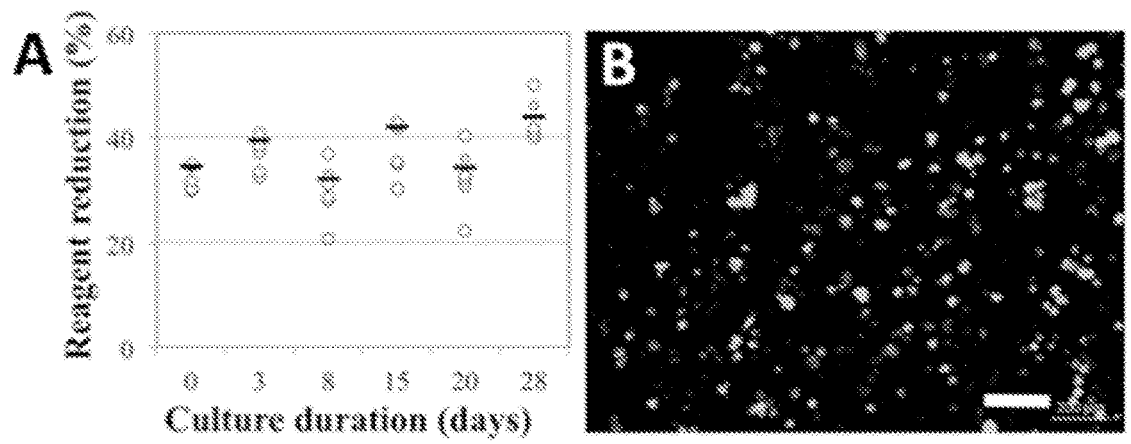
FIGS. 3A and 3B: 3A presents a graph characterizing in vitro cell proliferation using ALAMARBLUE® assay of AD-MSCs incorporated in the adhesive scaffolds (n=8). 3B presents a representative image of LIVE/DEAD staining of the AD-MSCs after 28 days of culture in the adhesive scaffolds. Scale bar=200 μm*=p<0.05 vs day 0.
Figure 4:
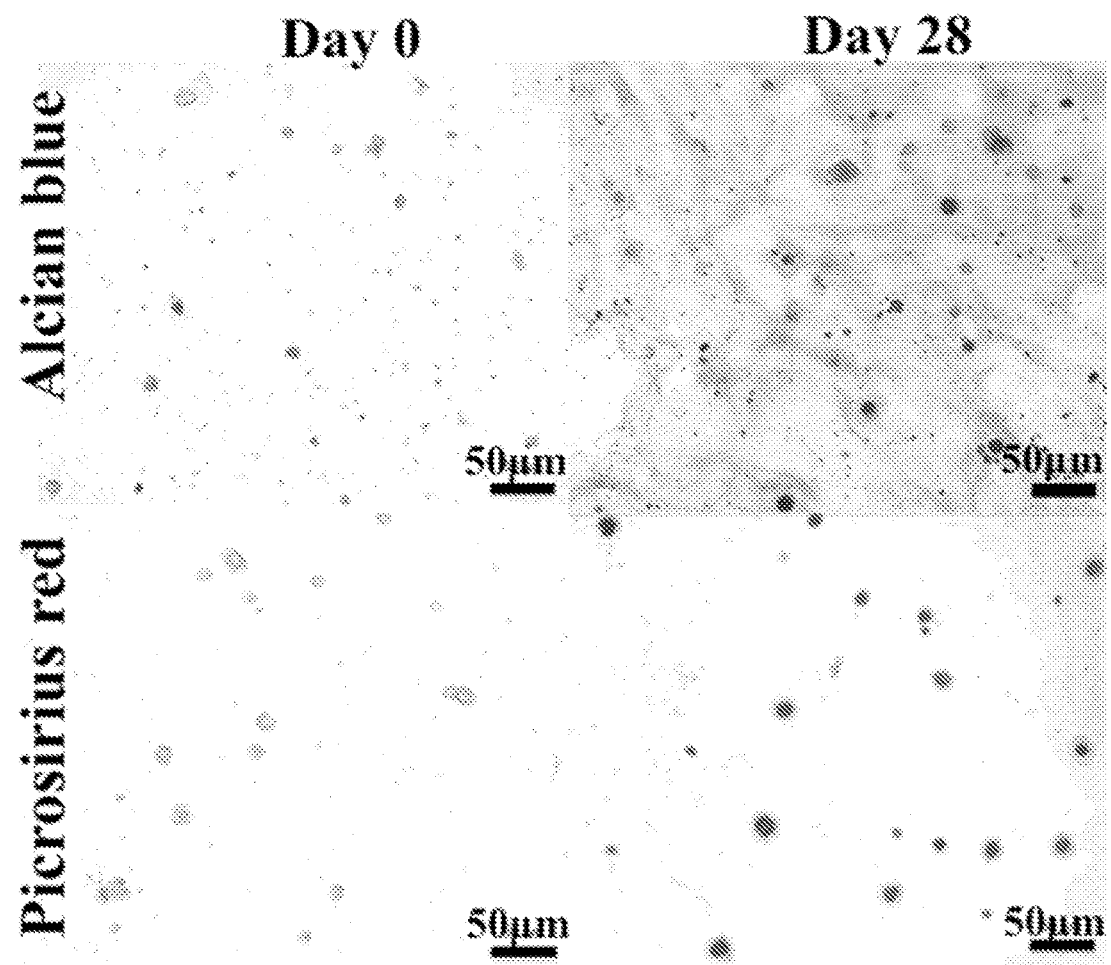
FIG. 4 presents representative histological images of AD-MSCs seeded in the adhesive immediately after encapsulation (day 0) and after 28 days in NP differentiating medium. Top panel, Alcian blue counterstained with safranin 0 (GAGs=light, cell nuclei=dark). Lower panel, Picrosirius red counterstained with fast green (collagen=dark, cell nuclei=light). There were appreciable increases in expression of GAG and collagen over the culture period. Scale bar=50 μm.

Commercial AD-MSCs (ATCC® PCS500011™) were expanded in monolayer culture to passage 6 to ensure sufficient cells were available. Cell-seeded adhesive polymer solutions were prepared at a density of $1\times10^6$ cells/mL. The AD-MSCs were encapsulated by heating the solutions to 37° C. The resulting solidified scaffolds (100 μL each) were cultured in NP differentiating medium supplemented with 50 ng/mL of GDF-6. The metabolic activity of the encapsulated cells was monitored using ALAMARBLUE® (Biorad, Oxford, UK). Percent reduction, calculated according to the manufacturer's instructions, immediately after encapsulation (day 0) and at days 3, 8, 15, 20 and 28, is reported in FIG. 3A. There was a significant increase (p=0.0001) in percent reduction between day 0 and 28, indicative of proliferation over the culture period. The LIVE/DEAD staining in FIG. 3B (Molecular Probes) performed on a gel at day 28 indicates that a majority of the encapsulated AD-MSCs remained viable throughout the culture period, shown by the fluorescent green staining. To confirm deposition of glycosaminoglycan (GAG) and collagen by the cells, one solidified gel from days 0 and Day 28 were each fixed in 4% formaldehyde for 1 hour, cryosectioned into 20 μm slices, placed onto gelatin-coated slides, and submersed for 15 minutes in 50 mM sodium citrate solution containing 4% formaldehyde to allow for selective dissolution of the scaffold components from the slide, eliminating non-specific background staining. The Alcian Blue and Picrosirus Red results in FIG. 4 indicate appreciable increases in matrix deposition between day 0 and day 28.

Ex Vivo Expulsion Testing.

Figure 5:
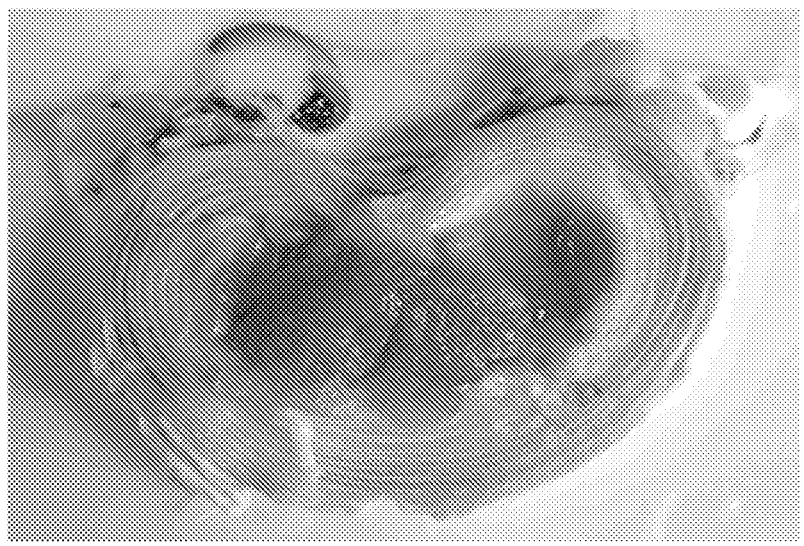
FIG. 5 presents a cross-section of a representative disc from expulsion testing. The polymer remained localized in the nuclear cavity during loading.

A solution of 5% (w/v) PNIPAAm-g-CS+50 mg/mL MPs (105 μm) was dyed blue to distinguish the implant from the rest of the porcine tissue. Adult lumbar porcine spines (male and female, approximately 1 year of age, 255-283 lbs., N=6) were used for testing. Spinal motion segments were isolated by removing surrounding connective tissue, bony processes, and spinal cord material. A partial nucleotomy was performed by inserting an 18 gauge needle through the annulus until the nuclear cavity was penetrated. With vacuum attached to syringe and needle, approximately 250-350 mg of NP material was aspirated from each sample, equating to approximately 50% of the NP. After partial nucleotomy, the discs were potted into polyurethane casting and warmed to physiological temperature. Disc specimens were injected with 4° C. polymer solution using an 18 gauge needle, until the syringe plunger did not depress further and the disc could not contain any more polymer solution. The disc specimens were then loaded in an MTS 831 elastomer testing machine at a rate of 5 mm/min to 500 lb (2.3 MPa) of axial pressure, equivalent to approximately three times the human body weight, scaled to porcine disc size. No implant expulsion or extrusion was observed in any of the six samples tested. Shown in FIG. 5 is the cross-section of a representative disc after testing, demonstrating that the implant was retained in the nuclear cavity during loading.

Lateral Bending Expulsion Tests.

Figures 6A, 6B:
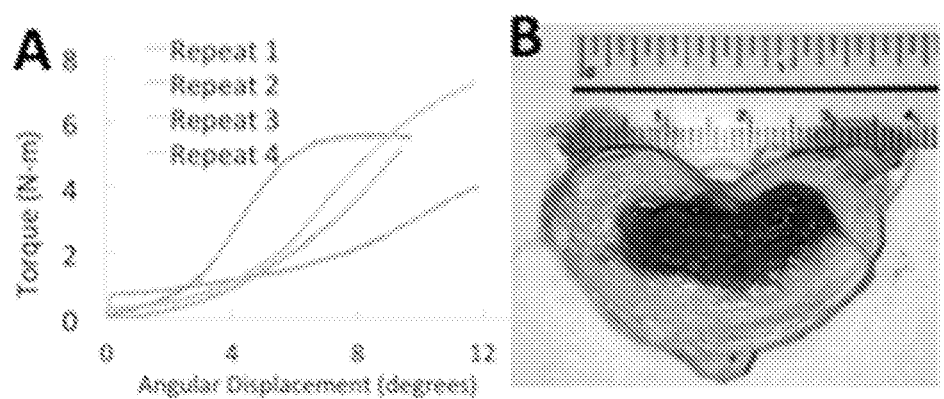
FIGS. 6A and 6B: 6A presents a graph of torque versus angular displacement curves for n=4 repeats of the high magnitude extrusion test. 6B presents a cross-section of a representative disc post-extrusion test demonstrates that the implant was retained in nuclear cavity during loading.

In this study, n=4 porcine discs were potted in polyurethane for testing. A partial nucleotomy was performed by inserting an 18-gauge needle through the AF with vacuum attached to syringe to remove approximately 50% of the NP tissue. Then, the discs were warmed to physiological temperature and injected with adhesive using an 18-gauge needle, until the syringe plunger did not depress further and the disc could not contain any more polymer solution. The specimens were loaded on an MTS 831 elastomer testing machine and an extrusion test was performed by applying a vertical displacement 1-inch from the center of the IVD to induce ±5° of lateral bending along the injury axis in displacement control for 10 cycles at a rate of 0.05 Hz. This was followed by a high magnitude test where the bending angle was continuously increased at a rate of 0.1°/sec on the side opposite to the injection site. The test was stopped manually when the maximum bending angle was reached due to geometric constraints of the tissue. The specimens were compressed to average maximum angle of 10.5±1.3° with no evidence of herniation. Illustrated in FIG. 6A are the torque versus angular displacement curves for the high magnitude tests. A representative cross-section of the disc in FIG. 6B demonstrates implant retention in the nuclear cavity during loading.

Biomechanics of Implanted Segments.

For this study, N=5 porcine discs were used for testing. An AF injury was created in each disc with a 2 mm punch and NP material was aspirated through the annular defect until 44±7% of the NP was removed. After partial nucleotomy, the discs were potted into polyurethane casting and warmed to physiological temperature. Simulated degeneration was mechanically induced by subjecting the IVD specimens to 50 cycles of compression from 0 to 400 lb (1.92±0.08 MPa) at 0.1 Hz. Disc specimens were injected with 4° C. polymer solution (5% (w/v) PNIPAAm-g-CS+50 mg/mL MPs (105 μm) using an 18 gauge needle, until the syringe plunger did not depress further and the disc defects could not contain any more polymer solution. Scissors were used to remove any excess gel that seeped outside of the annulus defect.

Figures 7A, 7B:
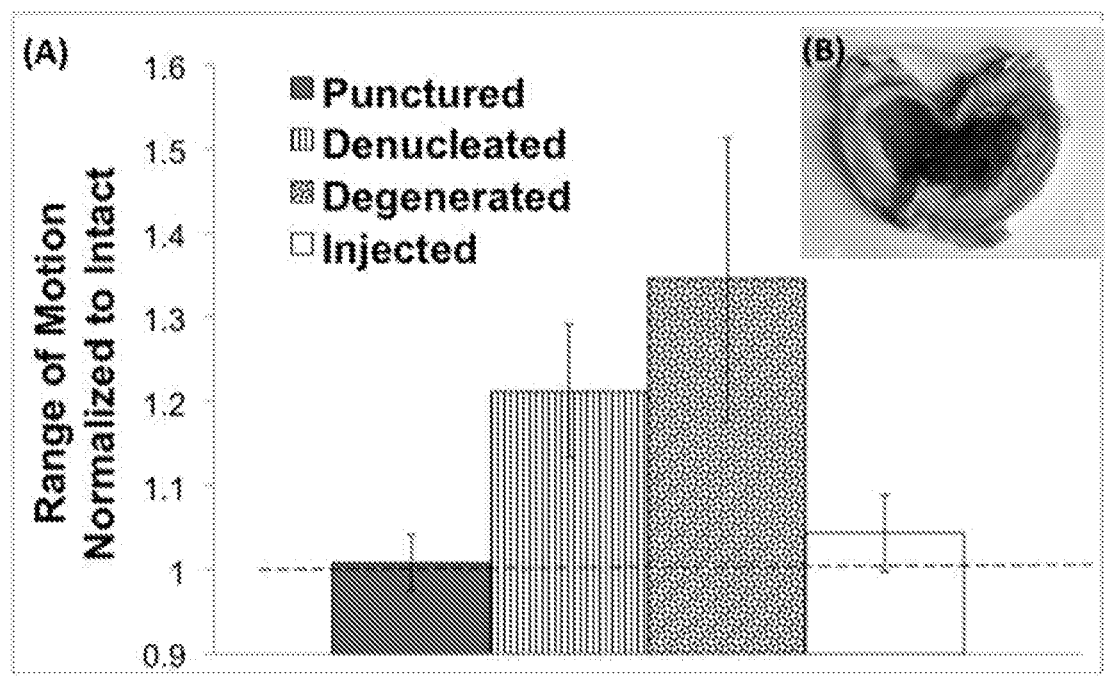
FIGS. 7A and 7B: 7A presents a graph of total range of motion (ROM) normalized to that of the intact condition for the punctured, partially denucleated, mechanically degenerated, and implanted specimens. The dotted line demonstrates restoration of the parameter relative to the intact condition post-injection of the adhesive. 7B presents a cross-section of a representative disc post-testing and demonstrates that the implant was retained in the nuclear cavity and annular defect during loading.

Biomechanical testing was performed by cycling 10 times to 40 lb (0.19±0.01 MPa) of tension and 150 lb (0.72±0.03 MPa) of compression at 0.75 Hz. Total range of motion (ROM) was calculated with the total peak-to-peak displacement in one direction and normalized to that of the intact disc. This loading scheme was performed on the intact disc, after puncture with the punch, after partial denucleation, after mechanical degeneration, and post-injection of the adhesive. The results are shown in FIG. 7A. Creating the 2 mm annulus injury resulted in a negligible increase in ROM. Approximately 405±58 mg of NP tissue was removed during nucleotomy, thus causing ROM to significantly increase (p<0.05). Mechanical degeneration induced through excessive compressive fatigue caused ROM to increase, yet not significantly (p>0.05), compared to the denucleated condition. Roughly 514±101 mg of the hydrogel composite was injected into the IVD and restored the ROM relative to the intact condition (p>0.05). Implant extrusion through the annular defect was also not observed during cyclical compressive loading. The cross-section in FIG. 7B, taken post-testing, demonstrates that the implant was retained in the nuclear cavity and AF defect during loading.

Elements Distinguishing the Present Technology from Others in the Field

The adhesive described herein is completely biocompatible and has been shown to support the survival of encapsulated cells. Many polymeric adhesives covalently bond rapidly with tissue and/or require high temperatures for cure, which would have limited utility for transferring viable cells into the IVD.

The adhesive described herein is also thermally sensitive, and thus does not require in situ polymerization to solidify into an elastic gel. This allows implant solidification in any area of the disc, whereas photopolymerizable materials may only be applied at a certain depth within the disc due to limited tissue penetration of a light source. Therefore the present materials are useful for multi-targeted healing of the IVD, in both the NP and AF.

Further, the adhesive described herein is injectable and forms a fully shape-filling gel. Some repair devices for the annulus are pre-formed and therefore not injectable, making it impossible to fill in irregularly shaped defects across all areas of the disc.

Other IVD repair technologies are designed to be applied in one area of the disc at a time, either the NP alone or the AF alone. The adhesive described herein is used to target any area of the disc (NP and AF simultaneously), rather than just one area.

The adhesive described herein also has a unique composition. Although alginate, in the form of microparticles, has traditionally been used in hydrogel formulations to achieve sustained drug delivery, the presently disclosed adhesive is the first use of alginate microparticles to enhance the adhesive nature of a polymer network.

The disclosure of every patent, patent application, and publication cited herein is hereby incorporated herein by reference in its entirety.

While the present subject matter has been disclosed with reference to specific embodiments, it is apparent that other embodiments and variations can be devised by others skilled in the art without departing from the true spirit and scope of the subject matter described herein. The appended claims include all such embodiments and equivalent variations.

What is claimed is:

1. A composition capable of forming a scaffold in situ at a intervertebral disc site, the composition comprising:
   (a) a biocompatible polymer at a concentration of from about 1 to about 90 weight percent based on the total weight of the composition;
   (b) a biocompatible solvent system in sufficient amount to solubilize the biocompatible polymer in sufficient degree to allow delivery of the composition to the intervertebral disc site, and further wherein the biocompatible polymer has a molecular weight or concentration sufficient to impart to the composition a viscosity that permits delivery to the intervertebral disc site; and
   (c) encapsulated material comprising insoluble alginate microparticles (MPs) as adhesion mediators.

2. The composition according to claim 1, wherein said composition has a suitable viscosity range for delivery at temperatures ranging from 1 to 40° C.

3. The composition according to claim 1, wherein said composition has a migration distance ranging from 2 mm to 50 mm.

4. The composition according to claim 1, wherein said biocompatible solvent is selected from the group consisting of water, ethanol, acetone, and mixtures of two or more thereof.

5. The composition according to claim 1, wherein the composition further contains a contrast agent.

6. The composition of claim 5, wherein the contrast agent is a water insoluble contrast agent.

7. The composition according to claim 6, wherein said water insoluble contrast agent is selected from the group consisting of tantalum, tantalum oxide, tungsten, and barium sulfate.

8. The composition of claim 1, wherein said polymer is selected from the group consisting of poly(ethylene oxide) (PEO), poly(propylene oxide) (PPOs), a copolymer of PEO and poly(lactic acid) (PLA), polyvinyl alcohol, acrylamide, polyurethane, poly(N-vinyl-2-pyrrolidone), acrylate, a copolymer of an acrylate with N-vinyl pyrrolidone, N-vinyl lactam, polyacrylonitrile, polyglycolic acid, polyethylene terephthalate, polybutyl lactose, polycaprolactone, D-polylactic acid, L-polylactic acid, polyglutamic, poly-L-lysine, poly-L-aspartic acid, poly(N-isopropylacrylamide), and any mixtures of two or more thereof.

9. The composition according to claim 1, wherein the polymer is poly(N-isopropylacrylamide) which is further grafted with chondroitin sulfate (PNIPAAm-g-CS).

10. A method of treating intervertebral disc defects, the method comprising administering into annulus fibrosus (AF) and nucleus pulposus (NP) sections of an intervertebral disc space of a mammal in need thereof a therapeutically effective amount of a composition which is capable of forming in situ a scaffold comprising a biocompatible polymer and insoluble alginate microparticles, wherein the biocompatible polymer has a molecular weight or concentration sufficient to impart to the composition a viscosity that permits delivery of the composition to the intervertebral disc site, wherein the method simultaneously repairs defects of the AF and the NP.

11. The method of claim 10, wherein the composition comprises poly(N-isopropylacrylamide) grafted with chondroitin sulfate (PNIPAAm-g-CS).

12. The method of claim 10, wherein the treatment reduces the need to surgically remove NP tissues during the procedure by at least 300 mg.

13. An intervertebral disc nucleus pulposus (NP) implant, comprising:
   (a) a load-bearing body comprising a load-bearing hydrogel comprising poly(N-isopropylacrylamide) grafted with chondroitin sulfate containing insoluble alginate microparticles as adhesive mediators, the load-bearing body surgically implanted in an intervertebral disc space; and
   (b) an outer shell or plug formed in situ around said outer surface of said load-bearing body after the load-bearing body is implanted within the intervertebral disc space;
   wherein said outer shell or plug comprises an amount of a biocompatible, biodegradable material sufficient to substantially or completely cover the load-bearing body; wherein said outer shell or plug is a different and separable material, and wherein said biocompatible, biodegradable material is injected partially or completely around the outer surface of said load-bearing body to form said outer shell or plug.

14. The disc nucleus pulposus implant of claim 13, wherein said injected biocompatible, biodegradable material is an adhesive material containing a contrast agent.

15. The disc nucleus implant of claim 13, wherein said load-bearing body comprises an elastic body sized to fill at least about 50% of the intervertebral disc space into which the implant is desired to be implanted.

16. The disc nucleus implant of claim 15, wherein said elastic body fills at least about 70% to 80% of the intervertebral disc space into which the implant is desired to be implanted.

17. The disc nucleus implant of claim 13, wherein said implant further includes a pharmacological agent.

18. The disc nucleus implant of claim 17 wherein said pharmacological agent comprises one or more members selected from the group consisting of contrast agents, growth factors, antibiotics, analgesics, anti-inflammatory drugs and steroids.

* * * * *